(12) United States Patent
Kwon et al.

(10) Patent No.: US 9,598,726 B2
(45) Date of Patent: Mar. 21, 2017

(54) METHOD FOR ENHANCING EFFICIENCY AND SENSITIVITY IN NUCLEIC ACID AMPLIFICATION FROM BIOLOGICAL MATERIALS USING IONIC LIQUIDS

(71) Applicant: Samsung Electronics Co., Ltd., Suwon-si, Gyeonggi-do (KR)

(72) Inventors: Sung-hong Kwon, Yongin-si (KR); Sung-min Chi, Hwaseong-si (KR); Kyu-youn Hwang, Seoul (KR); Joon-ho Kim, Seongnam-si (KR); Sun-ok Jung, Seongnam-si (KR); Sung-ouk Jung, Hwaseong-si (KR); Won-jong Jung, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 518 days.

(21) Appl. No.: 13/900,629

(22) Filed: May 23, 2013

(65) Prior Publication Data

US 2014/0030719 A1 Jan. 30, 2014

(30) Foreign Application Priority Data

Jul. 26, 2012 (KR) ........................ 10-2012-0081967

(51) Int. Cl.
*C12Q 1/68* (2006.01)
*C07H 21/04* (2006.01)

(52) U.S. Cl.
CPC .................................. *C12Q 1/6848* (2013.01)

(58) Field of Classification Search
CPC ........................ C12Q 1/6848; C12Q 2527/125
USPC ............................... 435/6.12, 91.2; 536/24.3
See application file for complete search history.

(56) References Cited

U.S. PATENT DOCUMENTS

| 6,992,182 | B1 | 1/2006 | Müller et al. |
| 7,459,548 | B2 | 12/2008 | Brolaski et al. |
| 2006/0121515 | A1 | 6/2006 | Otomo et al. |
| 2008/0299623 | A1 | 12/2008 | Kragl et al. |
| 2011/0244461 | A1 | 10/2011 | Tanigami et al. |

FOREIGN PATENT DOCUMENTS

| EP | 1736542 A1 | 12/2006 |
| JP | 2012-244916 A | 12/2012 |
| WO | WO 98/06877 A2 | 2/1998 |

OTHER PUBLICATIONS

Al-Soud et al., "Effects of Amplification Facilitators on Diagnostic PCR in the Presence of Blood, Feces, and Meat," *Journal of Clinical Microbiology*, vol. 38, No. 12, 4463-4470 (2000).
Stauffer et al., "Evaluation of four DNA extraction methods for the detection of *Tritvichomonas foetus* in feline stool specimens by polymerase chain reaction," *J. Vet Diagn Invest*, 20, 639-641 (2008).
Das et al., "Removal of real-time reverse transcription polymerase chain reaction (RT-PCR) inhibitors associated with cloacal swab samples and tissues for improved diagnosis of Avian influenza virus by RT-PCR," *J Vet Diagn Invest*, 21, 771-778 (2009).
Bessetti, "An Introduction to PCR Inhibitors," from http://www.promega.com (2007), pp. 1-2 (see European Search Report (item AG herein) for additional citation information).
Chevet et al., "Low concentrations of tetramethylammonium chloride increase yield and specificity of PCR," *Nucleic Acids Research*, 23(16): 3343-3344 (1995).
Mester et al., "Use of Ionic Liquid-Based Extraction for Recovery of *Salmonella* Typhimuium and *Listeria monocytogenes* from Food Matrices," *Journal of Food Protection*, 73(4): 680-687 (2010).
Shi et al., "Ionic liquids promote for amplification of DNA", *Chem. Communication*, 48: 5325-5327 (2012).
Wang et al, "Direct Extraction of Double-Stranded DNA Into Ionic Liquid 1-Butyl-3-methylimidazolium Hexafluorophosphate and Its Quantification", *Analytical Chemistry*, 79(2): 620-625 (2007).
European Search Report, European Application No. 13162867.9, dated Oct. 9, 2013.
Fukaya et al., "Superior Solubility of Polysaccharides in Low Viscosity, Polar, and Halogen-Free 1,3-Dialkylimidazolium Formates," BioMacromolecules, 7(12): 3295-3297 (2006).
Oikarinen et al., "PCR Inhibition in Stool Samples in Relation to Age of Infants," *J of Clinical Virology*, 44: 211-214 (2009).
Seoud et al., "Applications of Ionic Liquids in Carbohydrate Chemistry: A Window of Opportunities," BioMacromolecules,8(9): 2629-2647 (2007).

*Primary Examiner* — Jezia Riley

(74) *Attorney, Agent, or Firm* — Leydig, Voit & Mayer, Ltd.

(57) ABSTRACT

A method for amplifying a nucleic acid amplification in the presence of an ionic liquid that suppresses an inhibitor of nucleic acid amplification, particularly when in a biological material, and a composition useful for performing the method.

10 Claims, 6 Drawing Sheets

METHOD FOR ENHANCING EFFICIENCY AND SENSITIVITY IN NUCLEIC ACID AMPLIFICATION FROM BIOLOGICAL MATERIALS USING IONIC LIQUIDS

CROSS-REFERENCE TO RELATED APPLICATIONS

This application claims the benefit of Korean Patent Application No. 10-2012-0081967, filed on Jul. 26, 2012, in the Korean Intellectual Property Office, the disclosure of which is incorporated herein in its entirety by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 881 Byte ASCII (Text) file named "711540_ST25.txt," created on Feb. 1, 2013.

BACKGROUND

1. Field

The present disclosure relates to methods and compositions for nucleic acid amplification, particularly in the presence of nucleic acid amplification inhibitors.

2. Description of the Related Art

The amplification of nucleic acid from a biological material is affected by cellular lysis and the presence of various nucleic acid amplification inhibitory substances. Therefore, removing nucleic acid amplification inhibitors from biological materials improves nucleic acid amplification and assays related thereto, including molecular diagnostics.

Biological materials include, for example, mucus, blood, stool, and tissue samples from a subject. Nucleic acid amplification from a stool sample is particularly challenging, since sample variation is large and because nucleic acid amplification inhibitors, particularly heme, bilirubin, bile salt, and a variety of complex polysaccharides, may exist in the sample.

Nucleic acid amplification inhibitors can be removed from a biological material during pre-treatment or post-treatment of the sample. Removal of nucleic acid amplification inhibitors during pre-treatment of the sample (i.e., before preparation of the sample for nucleic acid amplification) is complicated, can be affected heavily by reactions, binding, and elution buffers used in the pre-treatment process, and may cause loss of target cells. Removal of nucleic acid amplification inhibitors during post-treatment of the sample (i.e., after preparation of the sample for nucleic acid amplification) may involve, for example, the addition of a nucleic acid amplification inhibitor removal substance to a polymerase chain reaction (PCR) master mix. No critical loss of target cells or DNA is observed in post-treatment. However, post-treatment is largely ineffective at removing nucleic acid amplification inhibitors. The use of various chemical substances (acetamide, betaine, dextran, DMSO, formamide, glycerol, PEG, PVP-10 etc.), detergents (tween, SDS etc.), and biomolecules (gp32 single strand binding protein, proteinase inhibitor etc.) have been studied but their effects are largely insufficient. Only BSA has been shown to have a slight effect on the removal of nucleic acid amplification inhibitors in some samples.

Therefore, improved method of amplifying nucleic acids from biological materials is needed.

SUMMARY

Provided is a method for amplifying a nucleic acid, particularly in the presence of a nucleic acid amplification inhibitor, by amplifying the nucleic acid amplification in the presence of an ionic liquid.

Also provided is a composition for amplification of a nucleic acid in the presence of a nucleic acid amplification inhibitor, the composition comprising an ionic liquid and a nucleic acid amplification mixture.

BRIEF DESCRIPTION OF THE DRAWINGS

These and/or other aspects will become apparent and more readily appreciated from the following description of the Examples, taken in conjunction with the accompanying drawings in which:

FIG. 2A is a graph of response unit (Rn) versus number of cycles, showing an amplification profile curve in relation to the effect of ionic liquid on PCR in stool sample; FIG. 2B is a graph of response unit (Rn) for various reaction conditions, showing a maximum Rn value calculated from an amplification profile curve in relation to the effect of ionic liquid on PCR in stool sample; FIG. 2C is an electrophoresis image showing an electrophoresis result of an amplified PCR product in relation to an ionic liquid effect on PCR in stool sample (A: ionic liquid+stool sample, B: absence of ionic liquid+stool sample, C: ionic liquid+genome DNA in buffer, D: absence of ionic liquid+genome DNA in buffer); FIG. 2D is a graph showing calculated density of amplified product from electrophoresis result (A: ionic liquid+stool sample, B: absence of ionic liquid+stool sample, C: ionic liquid+genome DNA in buffer, D: absence of ionic liquid+genome DNA in buffer).

FIG. 3A is a graph of response unit (Rn) versus number of cycles, showing an amplification profile curve for $10^2$ copies of genome DNA; FIG. 3B is a graph of response unit (Rn) versus number of cycles, showing an amplification profile curve for $10^1$ copies of genome DNA, and FIG. 3C is a graph of response unit (Rn) for various reaction conditions, showing the maximum Rn value calculated from FIG. 3A and FIG. 3B.

FIG. 4A is a graph of response unit (Rn) versus number of cycles, showing an amplification profile curve for $10^3$ copies of genome DNA; and FIG. 4B is a graph of response unit (Rn) for various reaction conditions, showing the maximum Rn value calculated from FIG. 4A.

DETAILED DESCRIPTION

Figure 1:
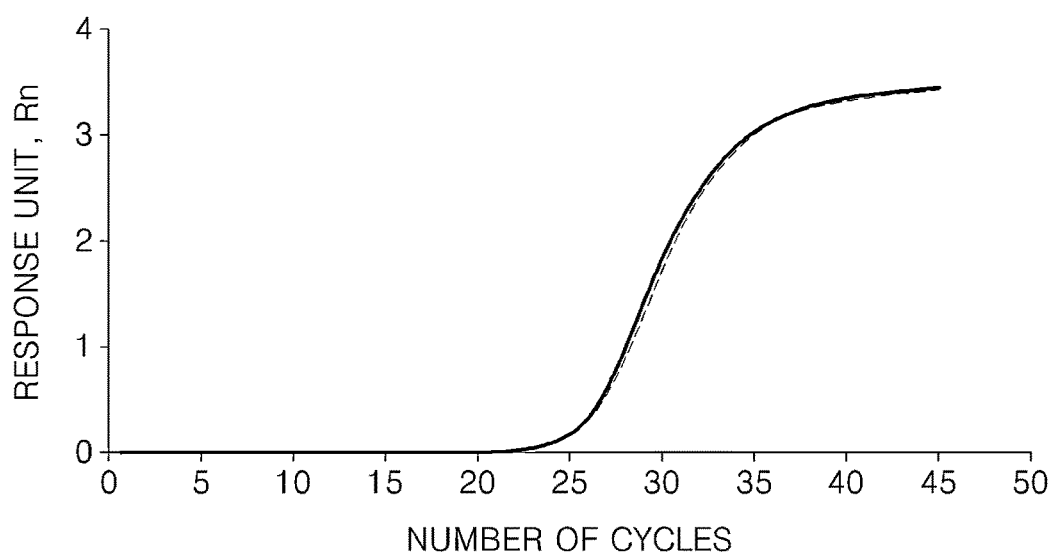
FIG. 1 is a graph of response unit (Rn) versus number of cycles, showing that the ionic liquid itself does not inhibit polymerase chain reaction (PCR)

Provided is a method for amplifying a nucleic acid, particularly in the presence of a nucleic acid amplification inhibitor, the method comprising amplifying the nucleic acid amplification in the presence of an ionic liquid. Nucleic acid amplification inhibitors are present in biological materials, and often contaminate samples containing nucleic acids that are amplification targets. Without wishing to be bound by any particular mechanism or theory, it is believed the ionic liquid suppresses the activity of the nucleic acid amplification inhibitor, directly or indirectly, and improves the reaction efficiency of nucleic acid amplification as compared to the same reaction (under the same conditions) in the absence of the ionic liquid.

The term "reaction efficiency" refers to the average number of nucleic acid amplification reactions per cycle (the average number of doublings per cycle) performed by polymerase chain reaction (PCR) under given conditions. The efficiency of PCR is influenced by the purity of materials, the amount of target substances, reaction conditions, the presence of reaction inhibitors, and so on. PCR is performed by repeating an adequate number of cycles, which ordinarily consist of denaturation to separate a DNA template into single strands, annealing of a primer to the template, and extension of the primer by polymerase. The higher the amplification efficiency, the less time it takes to reach a detectable level of amplification. For example, nucleic acid amplification efficiency can be understood as the time needed to amplify target nucleic acid to a detectable level.

The method may improve the reaction sensitivity or limit of detection of the amplification. The term "reaction sensitivity" or "limit of detection (LOD)" refers to the minimum amount of target nucleic acid that must be present to reliably detect and quantify under given PCR conditions. In real time-PCR (RT-PCR), the limit of detection is expressed as a maximum reaction unit (Max Rn) or a threshold cycle (Ct) value. The Ct value serves as a tool for calculation of the starting amount of nucleic acid template in a sample and represents the number of cycles at which a fluorescence signal prominently starts to increase from a base line (base signal).

The nucleic acid to be amplified may be present in a biological material. The term "biological materials" refers to any samples obtained or derived from a living organism. Thus, the biological materials include body tissues and body fluids, as well as any component thereof, particularly from mammals, including humans, or microorganisms. For example, the biological material may be a sample of feces, urine, blood, mucus, saliva, or sweat, or any component thereof (e.g., one or more partially or completely isolated cells or nucleic acid extract. The sample may be diluted, washed, dissolved, preserved, or partially or completely dehydrated, including freeze-dried. The sample may be used in the form obtained from the body, without first isolating or purifying the nucleic acid to be amplified from the sample. In some instances, it may be preferable to use complete sample, for instance, to prevent loss of sample volume and to save time/cost, especially if the sample quantity is small.

The ionic liquid can be added to the nucleic acid or biological material or to the mixture for nucleic acid amplification (i.e., nucleic acid amplification mixture) before combining the nucleic acid and the nucleic acid amplification mixture to perform the amplification, or the ionic liquid can be added to the combined reaction mixture (i.e., after the nucleic acid or biological material is combined with the nucleic acid amplification mixture. The terms "mixture for nucleic acid amplification," "nucleic acid amplification mixture" and "composition for nucleic acid amplification" refers to mixtures having all the components, aside from a nucleic acid template, necessary to perform nucleic acid amplification (i.e., a "master mix" or "pre mix"). Although referred to as a "mixture," some or all of the components might, in fact, be dissolved so as to be in solution. Thus, the term "mixture" in this context is intended to mean a combination of components, and is not limited to a physical mixture. The nucleic acid amplification mixture can include any substances typically used for target nucleic acid amplification, as well as any other component that does not substantially interfere with the nucleic acid amplification process. The composition may include, for example, nucleic acid polymerase, buffers, cofactors, and/or substrates. The nucleic acid polymerase may be DNA polymerase, RNA polymerase, reverse transcriptase, or a combination thereof. The nucleic acid polymerase may have strand displacement activity. For example, the nucleic acid polymerase may be a reverse transcriptase derived from retrovirus, e.g. HIV, MMLV, or AMV. The nucleic acid polymerase may not have 3'→5' exonuclease activity. The mixture may contain substances necessary for reverse transcription or PCR amplification. For example, the mixture may contain about 1 µM to 50 mM forward and reverse primers, buffer (e.g. 10 mM Tris HCl at a pH of about 8.0 to 9.0), about 40 mM KCl, about 1.5 mM $MgCl_2$, about 250 µM of each of the four types of dNTP, and about 0.5 to 1 U DNA polymerase. The mixture may be used at a high concentration, such as from ×2 to ×10, depending on a desired reaction amount and rate.

The term "ionic liquid" refers to a substance existing in a liquid state room temperature (e.g., 25° C.) despite ionic binding in the solution. An ionic liquid chemically resembles a salt; but, unlike a salt, it exists in liquid form at room temperature and can be used as a solvent. Ionic liquids are considered environment-friendly because they do not emit evaporative noxious substances, do not evaporate easily at room temperature, and are recyclable compared to organic solvents. Any suitable ionic liquid may be used. For example, suitable ionic liquids include those in which a cation of the ionic liquid comprises any of the following:

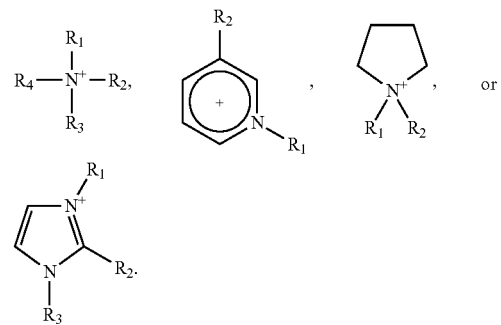

$R_1$ may be H, phenyl, $C_1$ to $C_{20}$ alkyl, $C_2$ to $C_{20}$ alkenyl, or $C_3$ to $C_{20}$ aryl; $R_2$ may be H, phenyl, $C_1$ to $C_{20}$ alkyl, $C_2$ to $C_{20}$ alkenyl, or $C_3$ to $C_{20}$ aryl; $R_3$ may be H, phenyl, $C_1$ to $C_{20}$ alkyl, $C_2$ to $C_{20}$ alkenyl, or $C_3$ to $C_{20}$ aryl; and $R_4$ may be H, phenyl, $C_1$ to $C_{20}$ alkyl, $C_2$ to $C_{20}$ alkenyl, or $C_3$ to $C_{20}$ aryl. Any of the foregoing ranges of carbon atoms specifically contemplates any and all subranges thereof. Thus, $C_1$-$C_{20}$ includes, for instance, ranges of one or more carbon atoms (e.g., two or more, three or more, four or more, five or more, six or more, seven or more, eight or more, nine or more, or ten or more carbons, etc.) and 20 or fewer carbons (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 5 or fewer carbons, etc. In certain embodiments, compounds with lower-alkyl substituents are used. Thus, for instance, one or more (two or more, three or more, or all) of $R_1$, $R_2$, $R_3$, and $R_4$ may be, independently, H, $C_1$ to $C_{10}$ alkyl (e.g., $C_1$ to $C_6$ alkyl or $C_1$ to $C_4$ alkyl), $C_2$ to $C_{10}$ alkenyl (e.g., $C_2$ to $C_6$ alkenyl or $C_2$ to $C_4$ alkenyl), or $C_3$ to $C_6$ aryl (e.g., phenyl). Suitable ionic liquids also include those in which a cation of the ionic liquid is

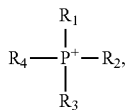

wherein each of $R_1$, $R_2$, $R_3$, and $R_4$ is, independently, H, $C_1$ to $C_6$ alkyl or $C_2$ to $C_6$ alkenyl. In addition, an anion of an ionic liquid may comprise, for example, halide, $SCN^-$, $BH_4^-$, $PF_6^-$, $CF_3COO^-$, $C_6H_5COO^-$, $(CF_3SO_2)_2N^-$, $CH_3OSO_3^-$, $(CN)_2N^-$, $NO_3^-$, $CH_3COO^-$, $CF_3SOO^-$, $(CH_3O)_2PO_2^-$, or $CH_3OSO_3^-$. By way of further illustration, the ionic liquid may comprise, for example, the following species of ionic bonding pairs:

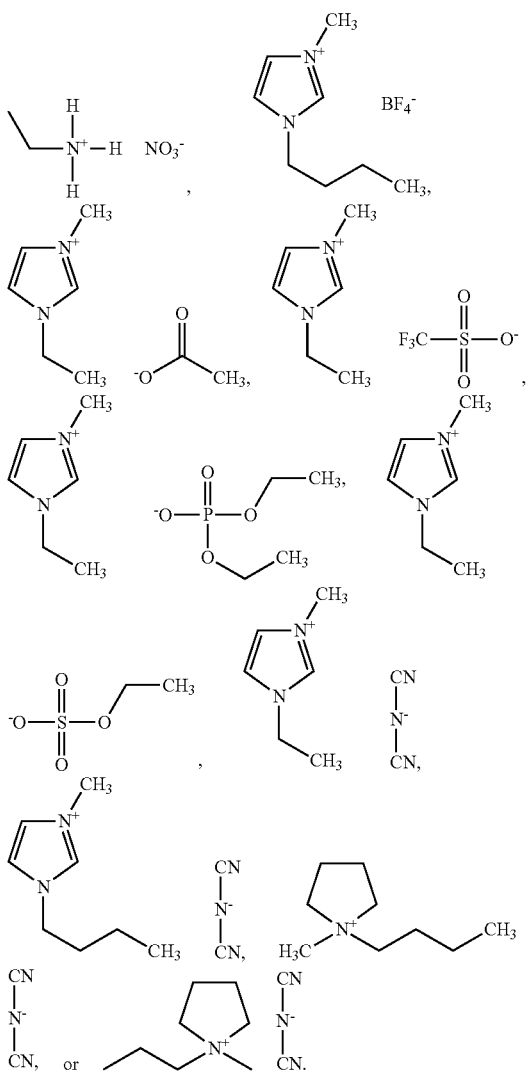

Additional specific examples of ionic liquids include tetra-(C1-C4 alkyl)-phosphonium compounds (e.g., tetrabutylphosphonium, tributylmethylphosphonium, and triethylmethylphosphonium compounds), such as tetrabutylphosphonium methanesulfonate; tetrabutylphosphonium tetrafluoroborate; tetrabutylphosphonium p-toluenesulfonate; tributylmethylphosphonium dibutyl phosphate; tributylmethylphosphonium methyl carbonate; tributylmethylphosphonium methyl sulfate; triethylmethylphosphonium dibutyl phosphate; and 3-(triphenylphosphonio)propane-1-sulfonate compounds (e.g., 3-(triphenylphosphonio)propane-1-sulfonate and 3-(triphenylphosphonio)propane-1-sulfonic acid tosylate).

According to one aspect of the method provided herein, the biological material containing the nucleic acids to be amplified and a mixture for nucleic acid amplification are prepared, and an ionic liquid is added to the biological materials, the mixture for nucleic acid amplification, or the reaction mixture comprising the biological materials and nucleic acid amplification reaction mixture.

To perform the amplification, a reaction mixture is prepared by combining the nucleic acid to be amplified, optionally in a biological material, and the mixture for nucleic acid amplification. The term "reaction mixture for nucleic acid amplification" refers to the reaction mixture that includes all compositions, in addition to a template, necessary to perform nucleic acid amplification.

The concentration of ionic liquid in the reaction mixture for nucleic acid amplification, or in an individual component of the reaction mixture to which the ionic liquid is added (e.g., the nucleic acid amplification mixture or biological material) may range from about 0.001% (v/v) to about 50% (v/v). For example, it may range from about 0.001% to about 30%, from about 0.001% to about 10%, or from about 0.001% to about 5%.

The reaction mixture for nucleic acid amplification may include one or more of bovine serum albumin (BSA), acetamide, betaine, dextran, DMSO, formamide, glycerol, polyethylene glycol (PEG), polyvinylpyrrolidone (PVP), Tween-20, Triton-X, sodium dodecyl sulfate (SDS), gp32 single strand binding protein, and a proteinase inhibitor. These may be added to the nucleic acid component (e.g., biological material) or the mixture for nucleic acid amplification (e.g., a PCR master mix) prior to preparing the reaction mixture, or may be added to the reaction mixture itself.

Amplification may be performed by any suitable technique. Term "nucleic acid amplification" refers to a technique by which specific nucleic acid sequences are amplified. Amplification, for example, may be amplification of DNA or RNA. The amplification may utilize thermal cycling or may be performed isothermally. The amplification may involve PCR, real-time PCR, nucleic acid sequence-based amplification (NASBA), ligase chain reaction (LCR), strand displacement amplification (SDA), rolling circle amplification (RCA), etc. The amplification method may be a RNA amplification method, such as reverse transcription or reverse transcription-PCR. "PCR" typically involves amplifying a target nucleic acid using a primer pair that specifically binds to a target and using a polymerase to extend or elongate the primers. The process generally involves repeating the steps of denaturation, annealing, and elongation. The term "annealing" may be used interchangeably with "hybridization." In addition, the amplification may be, for example, DNA amplification or RNA amplification. The amplification may be performed using real-time PCR, which is a method in which the generation of a PCR product is observed during every PCR cycle in real-time. The RT-PCR method analyzes a sample through detection and quantification of a fluorescence material reactive with a PCR product (e.g., a fluorescent probe).

It is believed that the ionic liquid used in conjunction with the presently described method suppresses the action of one or more nucleic acid amplification inhibitors that may be present in the reaction mixture. The term "nucleic acid amplification inhibitor" refers to a substance which inhibits nucleic acid amplification, or which inhibits the detection of an amplified product (e.g., an amplification signal does not appear despite amplification of the target, or the intensity of the signal is decreased). The nucleic acid amplification inhibitor may be a substance existing in a biological material, for example, bile acid, bile salts, polysaccharides, bilirubin, heparin, protein hydrolase, phenol compound, nuclease, polyamine, heme, hemin, collagen, melanin, eumelanin, myoglobin, proteinase, calcium ion, urea, hemoglobin, lactoferrin, immunoglobulin G, humic acid, glove powder, calcium chloride, ethylenediaminetetraacetic acid (EDTA), and/or $FeCl_3$.

The term "suppress" means to reduce the function or effect of a nucleic acid amplification inhibitor in the nucleic acid amplification reaction, partially or completely and directly or indirectly.

Also provided is a composition for nucleic acid amplification, which is believed to be particularly useful for amplifying nucleic acids in the presence of a nucleic acid amplification inhibitor, such as when the nucleic acid is in a biological material. The composition comprises an ionic liquid and a nucleic acid amplification mixture. The ionic liquid and nucleic acid amplification mixture, and all other aspects of the composition, are as described herein with respect to the method of amplifying a nucleic acid. Thus, the nucleic acid amplification mixture can comprise any component described with respect to the nucleic acid amplification mixture used in the method of amplifying a nucleic acid. Furthermore, the composition can comprise any other component described herein for use in the method of amplifying a nucleic acid, including those components used in the reaction mixture. Also, any composition described herein for the purposes of illustrating the method of amplifying a nucleic acid is considered to be an additional aspect of the invention.

The nucleic acid amplification composition may comprise any amount of ionic liquid sufficient to elicit the desired level of effect. For example, the concentration of ionic liquid of the nucleic acid amplification composition may range from about 0.001% (v/v) to 50% (v/v), such as about 0.001% to about 30%, from about 0.001% to about 10%, or from about 0.001% to about 5%.

According to preferred embodiments, the nucleic acid amplification method and composition described herein can be used to detect target microorganisms, cells, or genes rapidly, precisely and with high efficiency and sensitivity. For example, PCR efficiency and sensitivity can be improved by use of the methods and compositions described herein, and can be used for accurate molecular diagnosis by reducing or suppressing various nucleic acid amplification inhibitors existing in biological materials.

EXAMPLES

The following Examples further illustrate embodiments of the invention. However, the scope of the present invention is not limited to these Examples.

Example 1

The following Example illustrates amplification of a nucleic acid in the presence of an ionic liquid using PCR.

1-butyl-3-methylimidazolium tetrafluoroborate (BMITF) was used as an ionic liquid in a PCR reaction mixture as follows:
$10^3$ copies of genome DNA,
1×PCR master mix, and
0.5% (v/v) ionic liquid or distilled water
The PCR master mix included primer/probe, z-taq polymerase (TaKara), dNTP, and z-taq buffer.

```
Forward primer:
                                      (SEQ ID NO: 1)
5'-CGGGTTGTGTTAATTGAAC-3'

Reverse primer:
                                      (SEQ ID NO: 2)
5'-GAAGCGGCTGAAAAAACCGCA-3'

Probe:
                                      (SEQ ID NO: 3)
5'-AGAGCATTTAAGATTATGCG-3'
```

For PCR, TMC 1000 (Samsung) was used and a total of 45 cycles of PCR were performed, having 1 second at temperature sensitivity of 95° C., and 5 seconds at 60° C. per cycle.

The Rn by the number of PCR cycles represented by the amplification profile curve is shown in FIG. 1 (thick solid line: including ionic liquid of 0.5% (v/v), dashed line: not including ionic liquid).

As shown in FIG. 1, ionic liquid itself does not impose any inhibitory PCR effect.

Example 2

The following example illustrates the effect of ionic liquid on the amplification efficiency or sensitivity of PCR of nucleic acids from a stool sample.

The final reaction concentration of the PCR reaction mixture used is shown below:
Stool elution sample,
$10^3$ copies of genome DNA,
1×PCR master mix, and
0.5% (v/v) ionic liquid or distilled water.
The compositions of PCR master mix and conditions for PCR were as described in Example 1.

Figure 2A:
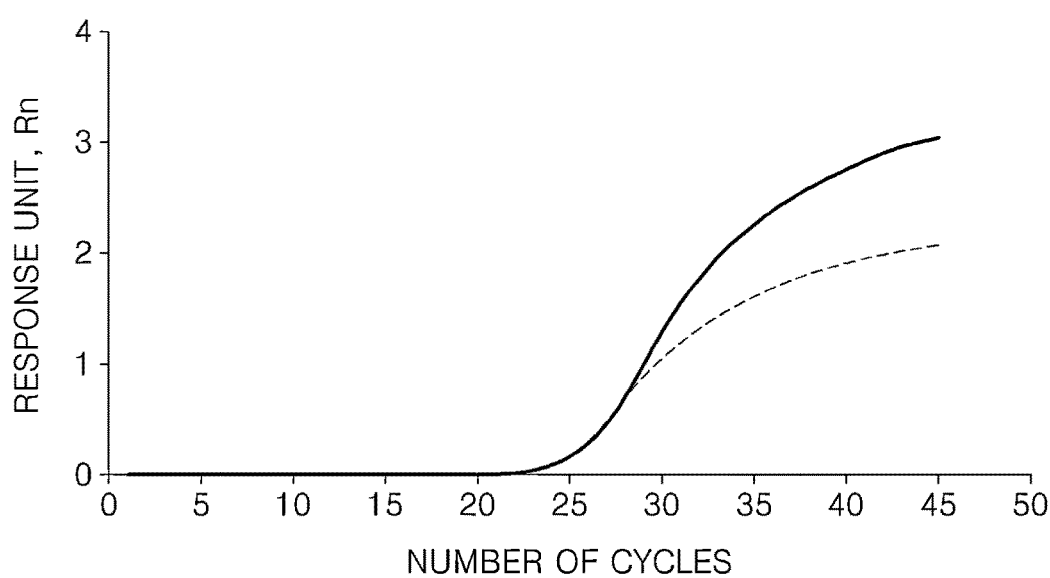
FIG. 2A to 2D show the effects of an ionic liquid on PCR amplification.
Figure 2B:
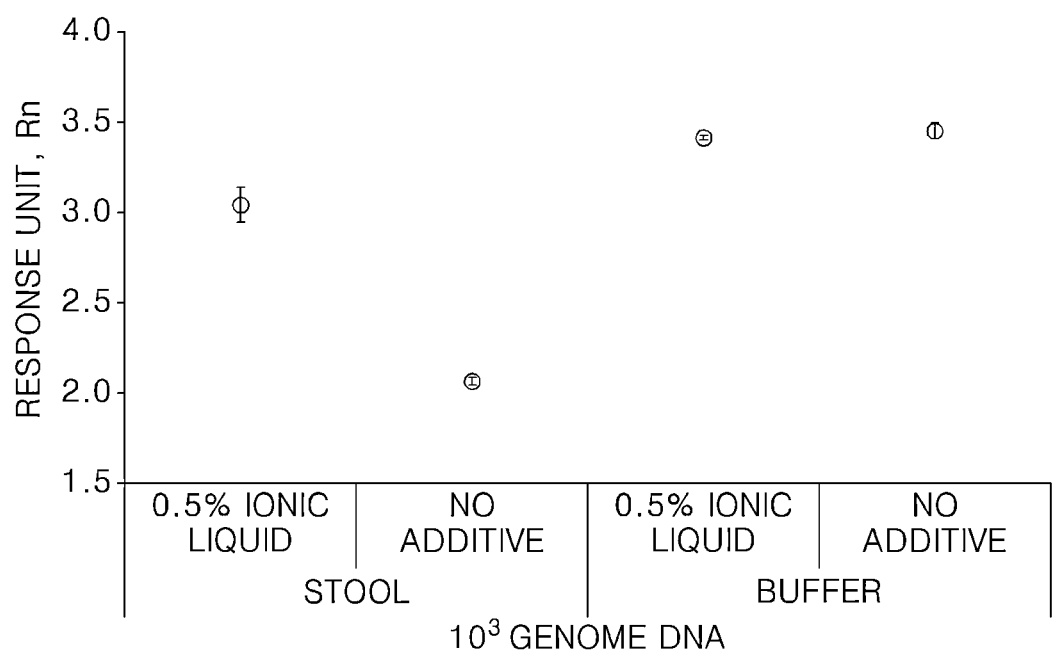

As shown in FIG. 2A, the amplification profile curve indicating Rn with respect to the number of PCR cycles was obtained, and the maximum Rn value was calculated from the curve (thick solid line: including ionic liquid of 0.5% (v/v), dashed line: not including ionic liquid).

Figure 2C:
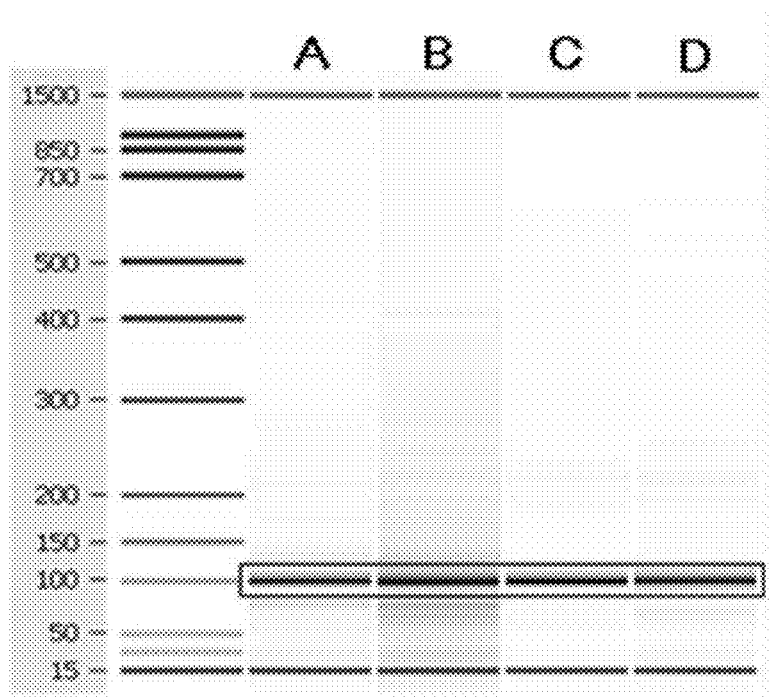
Figure 2D:
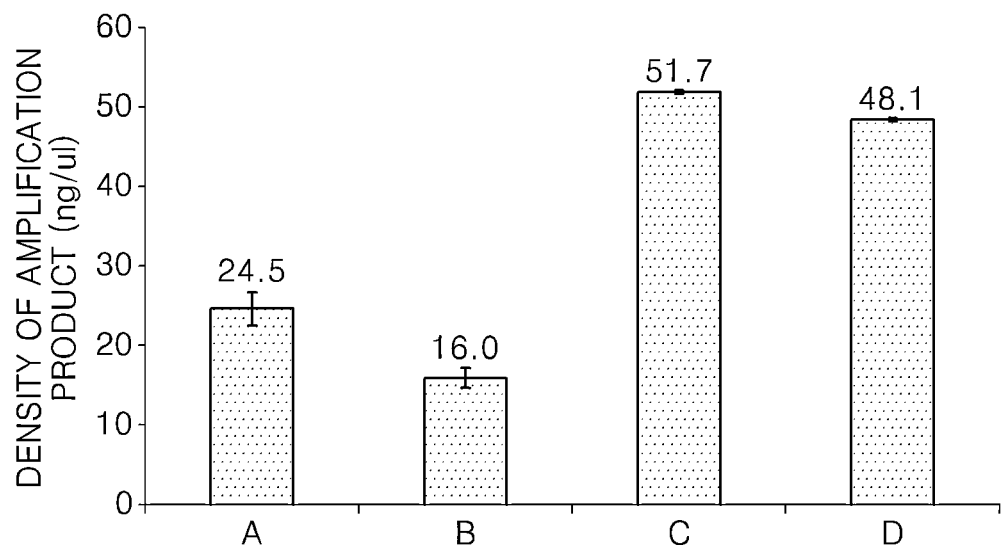

The amplification product produced by PCR was separated by electrophoresis using agarose gel, and the quantity of the target amplification product was compared (Bioanalyzer 2100, Agilent). FIG. 2C shows an electrophoresis result of an amplification product, and the quantity of yielded amplification product is shown in FIG. 2D (A: ionic liquid+stool sample, B: absence of ionic liquid+stool sample, C: ionic liquid+genome DNA in buffer, D: absence of ionic liquid+genome DNA in buffer).

As shown in FIG. 2A to FIG. 2D, the increase of the maximum Rn value of the PCR amplification profile curve can be confirmed when ionic liquid was used. The use of ionic liquid increases the efficiency of PCR amplification. It is believed that the increase in efficiency is due to the ionic liquid suppressing PCR inhibitors in the sample.

Example 3

The following Example illustrates the effect of ionic liquid on PCR of a stool sample containing a small amount of target DNA.

It was examined whether the presence of ionic liquid in fecal sample containing small amounts of target DNA increases the amplification efficiency and sensitivity of PCR.

The final reaction concentration of the used PCR reagent is shown below: Stool elution sample,
$10^2$ or $10^1$ copies of genome DNA,
1×PCR master mix, and
0.5% (v/v) ionic liquid or distilled water.

The compositions of PCR master mix and conditions for PCR were as described in Example 1.

Figure 3A:
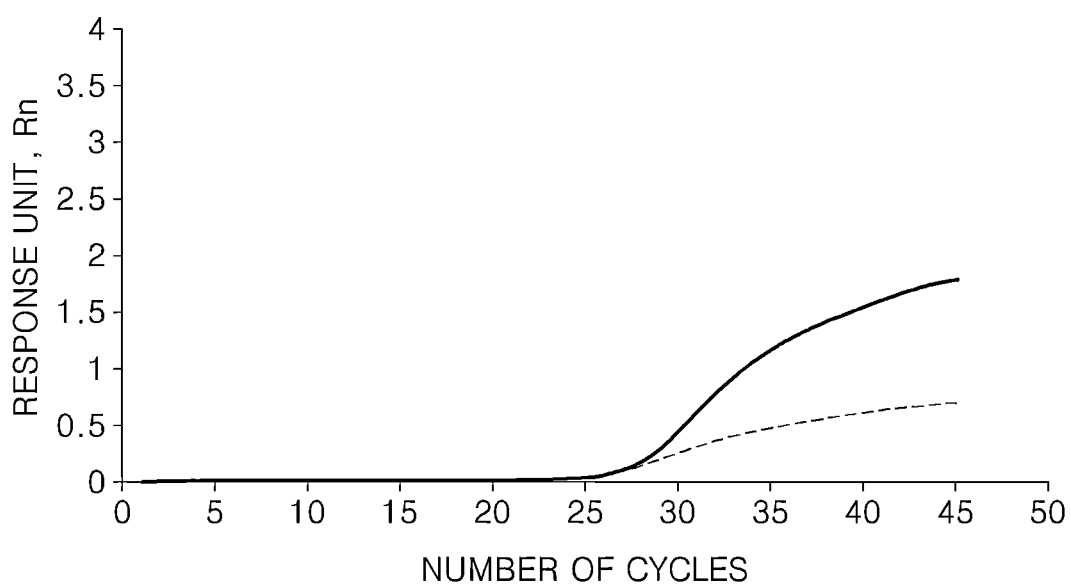
FIG. 3A to FIG. 3C show the effects of ionic liquid on PCR in stool sample.
Figure 3B:
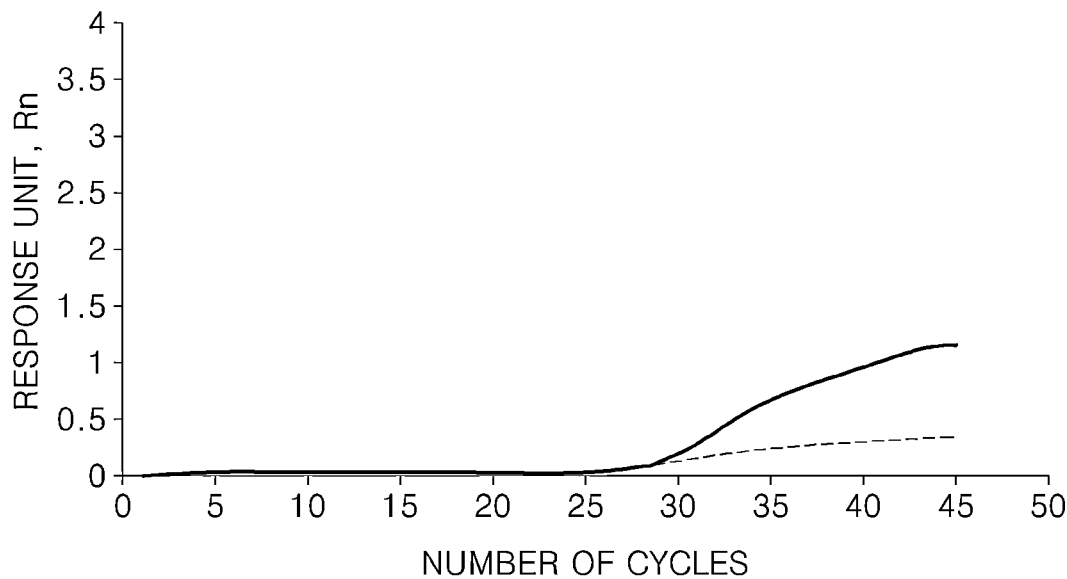

An amplification profile curve, represented as Rn with respect to the number of PCR cycles, was obtained and is shown in FIG. 3A (amplification profile curve of $10^2$ copies of genome DNA) and FIG. 3B (amplification profile curve of $10^1$ copies of genome DNA) (thick solid line: including ionic liquid of 0.5% (v/v), dashed line: not including ionic liquid). Moreover, the maximum Rn value yielded from FIG. 3A and FIG. 3B is shown in FIG. 3C.

Figure 3C:
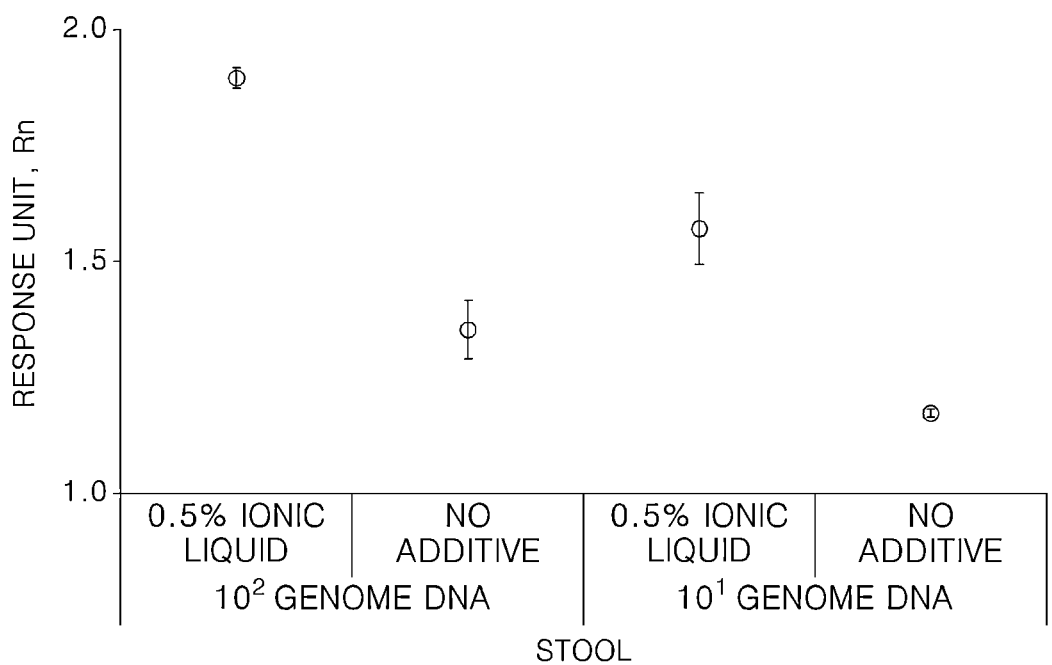

As shown in FIG. 3A to FIG. 3C, whereas an adequate Ct value could not be obtained without ionic liquid usage for low concentration target DNA, the Ct value was measurable when ionic liquid was used. The PCR amplification efficiency and sensitivity is low due to the influence of PCR inhibitors in fecal samples, but LOD is improved as the PCR amplification efficiency and sensitivity becomes superior due to the use of ionic liquid.

Example 4

The following Example compares the effects of BSA and ionic liquid on amplification efficiency and sensitivity of PCR of a stool sample.

The final reaction concentration of the PCR reagent is shown below:
$10^3$ copies of genome DNA,
1×PCR master mix, and
0.5% (v/v) ionic liquid, 0.1% (v/v) BSA or distilled water.

The master mix of the PCR composition and conditions for PCR were as described in Example 1.

Figure 4A:
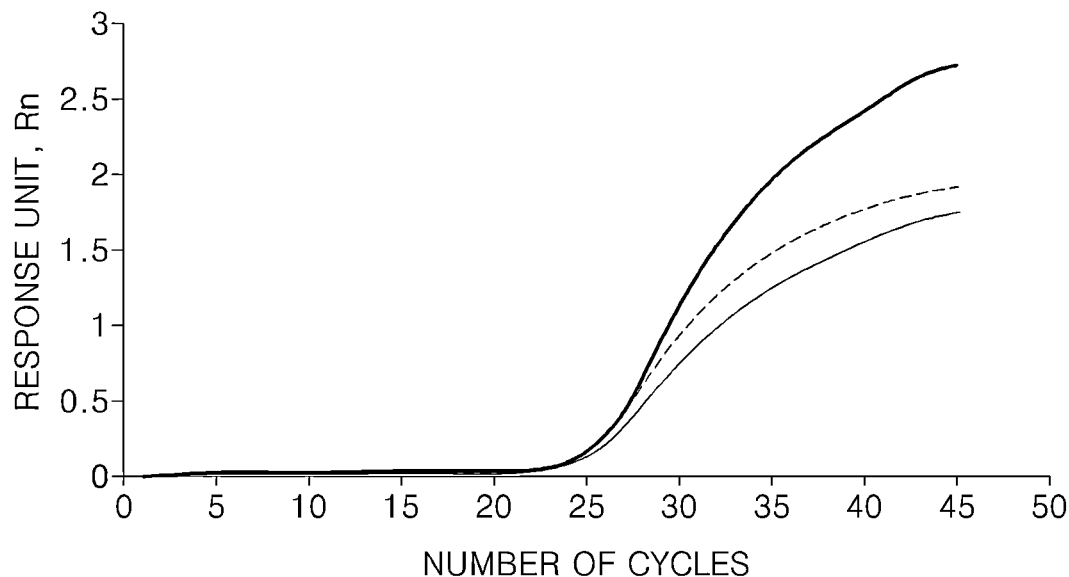
FIG. 4A to FIG. 4B show the effects of ionic liquid or BSA on PCR in a fecal sample.
Figure 4B:
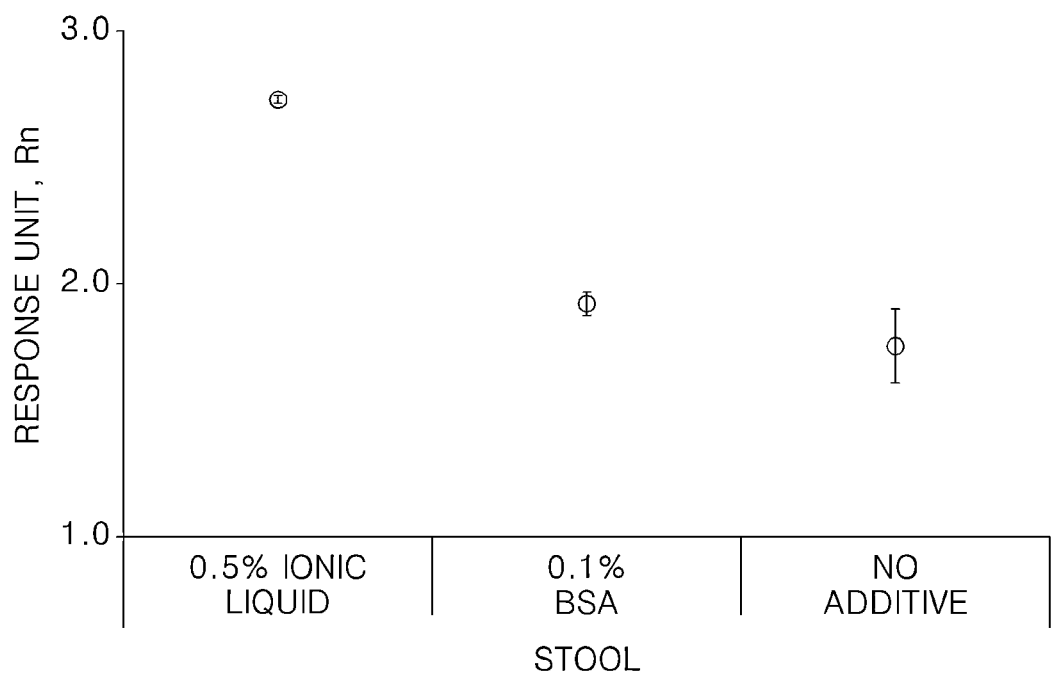

An amplification profile curve, represented as Rn with respect to the number of PCR cycles, was obtained and is shown in FIG. 4A, and the maximum Rn value yielded from FIG. 4A is shown in FIG. 4B. (thick solid line: including ionic liquid of 0.5% (v/v), dashed line: not including ionic liquid).

As shown in FIG. 4A and FIG. 4B, only use of BSA, which is commonly used to remove or suppress a PCR inhibitor in a stool sample, is compared. The Rn value increased by at least 1 in experiment using ionic liquid. Therefore, it was confirmed that the PCR inhibitor, which could not removed by BSA alone, could be removed by ionic liquid.

Example 5

The following Example illustrates screening of ionic liquids for removal or suppression effect upon PCR inhibitors.

PCR was performed by changing the ionic liquid. The compositions of the PCR reaction mixture used and the PCR conditions were as described in Examples 1 and 2.

The results are presented in the table, below, in which ΔRn is the difference between the maximum Rn value in the presence of ionic liquid and the Rn value in the absence of the ionic liquid.

As shown in the table, nucleic acid amplification inhibitor removal or suppression effects are observed in the order of BMITF>EMIDC>BMPDC>MPPDC>BMIDC.

| Ionic Liquid | Formula | Concentration % (v/v) | ΔRn |
| --- | --- | --- | --- |
| 1-ethyl-3-methylimidazolium dicyanamide (EMIDC) | 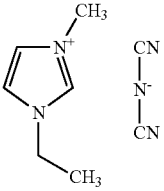 | 0.50<br>0.25<br>0.10<br>0.00 | 1.2<br>0.7<br>0.2<br>0.0 |
| 1-ethyl-3-methylimidazolium acetate (EMIA) | 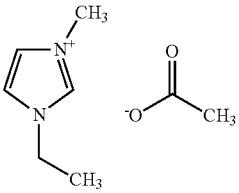 | 0.50<br>0.25<br>0.10<br>0.00 | 0.3<br>0.0<br>−0.3<br>0.0 |
| 1-ethyl-3-methylimidazolium triflate (EMITF) | 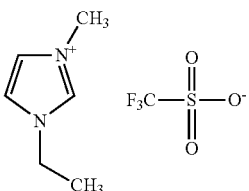 | 0.50<br>0.25<br>0.10<br>0.00 | 0.6<br>0.3<br>−0.1<br>0.0 |

-continued

| Ionic Liquid | Formula | Concentration % (v/v) | ΔRn |
|---|---|---|---|
| 1-ethyl-3-methylimidazolium ethyl sulfate (EMIES) | | 1.00<br>0.50<br>0.10<br>0.00 | 0.3<br>0.2<br>−0.1<br>0.0 |
| 1-butyl-3-methylimidazolium dicyanamide (BMIDC) | | 0.50<br>0.25<br>0.10<br>0.00 | 1.0<br>0.4<br>0.0<br>0.0 |
| 1-methyl-1-propylpyrrolidinium dicyanamide (MPPDC) | | 0.50<br>0.25<br>0.10<br>0.00 | 1.0<br>0.5<br>0.2<br>0.0 |
| 1-butyl-1-methylpyrrolidinium dicyanamide (BMPDC) | | 0.50<br>0.25<br>0.10<br>0.00 | 1.0<br>0.6<br>0.2<br>0.0 |
| 1-ethylammonium nitrate (EAN) | | 0.50<br>0.25<br>0.10<br>0.00 | −0.30<br>0.8<br>0.2<br>0.0 |
| 1-butyl-3-methylimidazolium tetrafluoroborate (BMITF) | | 1.00<br>0.50<br>0.00 | 0.8<br>1.0<br>0.0 |
| 1-ethyl-3-methylimidazolium diethylphosphate (EMIDP) | | 2.00<br>1.00<br>0.50<br>0.00 | −0.3<br>0.2<br>0.0<br>0.0 |
| Trihexyltetradecyl phosphonium dicyanamide (TTPDC) | | Could not be used due do layer separation in aqueous solution | |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for amplifying a nucleic acid, the method comprising: amplifying a nucleic acid in the presence of an ionic liquid and a nucleic acid amplification inhibitor, wherein the ionic liquid suppresses the inhibitory effect of the nucleic acid amplification inhibitor, wherein the ionic liquid comprises at least one cation selected from the group consisting of:

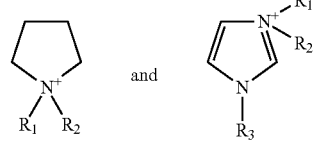

wherein each of $R_1$, $R_2$, and $R_3$ is, independently, H or a $C_1$ to $C_4$ alkyl;
and wherein the ionic liquid comprises at least one anion selected from the group consisting of $BF_4^-$ and $(CN)_2N^-$.

2. The method of claim 1, wherein the nucleic acid is in a biological material comprising a nucleic acid amplification inhibitor.

3. The method of claim 1, further comprising
adding an ionic liquid to at least one of a biological material comprising a nucleic acid for amplification or a nucleic acid amplification mixture;
combining the biological material and the nucleic acid amplification mixture to provide a reaction mixture for nucleic acid amplification; and

SEQUENCE LISTING

<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Synthetic

<400> SEQUENCE: 1
cgggttgtgt taattgaac                                           19

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
gaagcggctg aaaaaaccgc a                                        21

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
agagcattta agattatgcg                                          20 amplifying the nucleic acid,
wherein the biological material comprises a nucleic acid amplification inhibitor and the ionic liquid suppresses the inhibitory effect of the nucleic acid amplification inhibitor.

4. The method of claim 1, wherein the ionic liquid is selected from the group consisting of

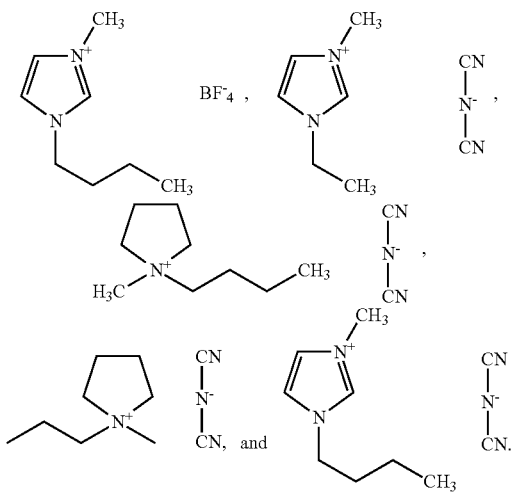

5. The method of claim 2, wherein the biological material comprises a body fluid or tissue, which is, optionally, diluted or dissolved, preserved, washed, or freeze-dried.

6. The method of claim 5, wherein the biological material comprises feces, urine, blood, mucus, saliva, or sweat, body fluid, and or tissue.

7. The method of claim 1, wherein the concentration of the ionic liquid is about 0.001% (v/v) to about 50% (v/v).

8. The method of claim 1, wherein the nucleic acid amplification inhibitor comprises bile acid, bile salts, polysaccharides, bilirubin, heparin, protein hydrolase, a phenol compound, nuclease, polyamine, heme, hemin, collagen, melanin, eumelanin, myoglobin, proteinase, calcium ion, urea, hemoglobin, lactoferrin, immunoglobulin G, humic acid, glove powder, calcium chloride, ethylenediaminetetraacetic acid (EDTA), $FeCl_3$, or a combination thereof.

9. The method of claim 1, wherein the amplification is performed in the presence of bovine serum albumin (BSA), acetamide, betaine, dextran, dimethyl sulfoxide (DMSO), formamide, glycerol, polyethylene glycol (PEG), polyvinylpyrrolidone (PVP)-10, Tween-20, Triton-X, sodium dodecyl sulfate (SDS), gp32 single strand binding protein, proteinase inhibitor, or combination thereof.

10. The method of claim 1, wherein the amplification is performed using one or more of PCR, real-time PCR, nucleic acid sequence-based amplification (NASBA), ligase chain reaction (LCR), strand displacement amplification (SDA), rolling circle amplification (RCA), or reverse-PCR.

* * * * *